United States Patent [19]

Khan

[11] Patent Number: 5,484,767
[45] Date of Patent: Jan. 16, 1996

[54] SUBSTANTIALLY PURE STEROIDOGENESIS INDUCING PROTEIN AND USES THEREOF

[76] Inventor: Shafig A. Khan, Charles H. Best Institute, 112 College Street, Toronto, Ontario, Canada, M5G 1L6

[21] Appl. No.: 709,073

[22] Filed: May 30, 1991

[51] Int. Cl.$^6$ .......................... A01N 37/18; A61K 38/00; C07K 5/00; C07K 17/00
[52] U.S. Cl. ................. 514/2; 514/12; 530/324; 435/268
[58] Field of Search .................. 514/2, 12; 530/324; 435/268

[56] References Cited

U.S. PATENT DOCUMENTS

| | | | |
|---|---|---|---|
| 4,196,123 | 3/1980 | Rosemberg | 530/324 |
| 4,945,055 | 7/1990 | Kuehl et al. | 435/268 |

OTHER PUBLICATIONS

Berne et al Physiology (CV Mosby Co. 2nd ed. 1988) 986–997, 1017–1018.
Khan et al., Acta Endocrinologica (1988) vol. 118 283–293.

*Primary Examiner*—Jill Warden
*Assistant Examiner*—A. M. Davenport
*Attorney, Agent, or Firm*—Felfe & Lynch

[57] ABSTRACT

A substantially pure steroidogenesis inducing protein ("SIP") is disclosed. The protein is characterized by a molecular weight of 60 kd as determined by SDS-PAGE, a pI of 4.7 to 4.9 and a non cAMP linked mechanism of action. The protein stimulates production of sex and adrenal cells, and also stimulates the production of various steroid hormones. The use of the pure protein in various therapeutic contexts as well as pharmaceutical compositions for therapy are also disclosed.

9 Claims, 6 Drawing Sheets

SUBSTANTIALLY PURE STEROIDOGENESIS INDUCING PROTEIN AND USES THEREOF

In mammals, the function of sex organs is controlled by the secretion of pituitary gonadotropins, the luteinizing hormone (LH) and the follicle stimulating hormone (FSH). In addition, the sex organs themselves produce paracrine and autocrine regulating factors which either inhibit or stimulate the effect of FSH and LH. (Sharpe (1986), Clin. Endocrinol. Metab. 15, 185–207); Hsueh (1986), Clin. Endocrinol. Metab. 15, 117–134).

Several such factors were found in testes and ovaries. It is known that extracts from rat ovaries contain at least two factors which influence the effect of LH. One of these factors inhibits the binding of LH to its receptor and, hence, reduces progesterone synthesis whereas the other one stimulates steroid production in Leydig cells of rats (Yang et al. (1979), Endocrinology 104, 552–558). A factor which stimulates steroid production in Leydig cells was also found in bovine follicle fluid (Risbridger et al. (1987), in Morphological Basis of Human Reproductive Function, Plenum Press, New York, pages 63–64).

Khan et al. (1988) Acta Endocrinol. 118, 283–293 also detected activity in human follicle fluid from ovaries. This fluid heavily stimulated testosterone production in Leydig cells. The active molecule is obviously a protein since the active fraction can be precipitated with ammonium sulfate, is lost by heating up to 80° to 100° C., and, based on gel chromatography of the raw extract, has an approximate molecular weight of 30 to 50 kDa. The active factor is chemically and immunologically distinct from LH as well as from human chorionic gonadotropin (hCG) and human menopause gonadotropin (hMG).

Therapeutic treatments make use of different gonadotropins. In male subjects, for example, hCG is used in combination with hMG for initiating and maintaining spermatogenesis in hypogonadotropic hypogonadism. Combinations of hCG with hMG have been used for treating idiopathic oligozoospermia. The results, however, have been disappointing (Knuth et al. (1987) J. Clin Endocrinol. Metab. 65, 1081–1087). Further, sterile women who are resistant to the ovulation-triggering pharmaceutical preparation Clomifen are treated for the formation of multiple follicles with a combination of hCG and hMG. However, this therapeutic treatment is not satisfactory since it is difficult, expensive and may even be risky when not carried out by an expert. Finally, no satisfying treatment is known for another illness, the so called "Resistant Ovarium Syndrome" where the follicles do not respond to FSH. It is therefore important to find new therapeutically useful gonadotropin hormones.

It is hence an object of the invention to provide a new protein hormone which can be used as a therapeutic alternative to known hormones such as LH, FSH, hCG, and hMG and in combination therewith.

This object is accomplished by a substantially pure human steroidogenesis inducing protein (SIP) obtained from human follicle fluid. It is a hormone with a molecular weight of 60 kD (SDS-PAGE) and an isoelectric point between 4.7 and 4.9. It stimulates hormone production of sex cells and adrenal cells wherein this stimulation is transmitted via a mechanism which does not involve the cAMP cycle.

The hormone of the invention is present in testes and in follicles. Its apparent molecular weight after gel chromatography ranges between 30 and 50 kD whereas in buffers of a low ionic strength, it has a molecular weight of 60 kD. SDS-PAGE analysis of highly purified SIP shows a molecular weight of 60 kD under reducing as well as non-reducing conditions.

SIP is the first protein-hormone to stimulate steroid production without the involvement of the cAMP cycle. It affects the mitochondria and can stimulate testosterone production in Leydig cells, progesterone production in granulosa cells and corticoid formation in adrenal cells. Its activity is very high exceeding presently known factors by approximately 10 to 15 times. Further, it can stimulate the proliferation of immature Leydig cells.

Moreover, it stimulates the cleavage of cholesterol side chains in the mitochondria of Leydig cells.

In female subjects, SIP can be detected shortly before ovulation. However, the hormone cannot be detected at the beginning of the female reproductive cycle.

Another subject of the invention is a process for obtaining the hormone of the invention wherein human follicle fluid (hFF) is collected and the hormone is obtained therefrom by means of concentration. hFF of female subjects, where the women were previously treated with gonadotropic hormones, is a suitable starting material. First, the cellular components of hFF are preferably separated and the supernatant containing the hormone is prepurified by ammonium precipitation at 80% saturation and dialysis. The purification of the hormone was continued with standard biochemical methods such as gel chromatography and/or gel filtration, concentration, affinity chromatography, ion exchange chromatography and again gel chromatography. The bioactive fractions can be determined after each purification stage by appropriate tests, e.g. stimulating testosterone production in Leydig cells. It is thus possible to purify the hormone of the invention to homogeneity.

SIP, the hormone of the invention, is of extraordinary clinical importance. Another subject of the invention is a pharmaceutical preparation which contains the hormone of the invention in addition to a regular pharmaceutically acceptable carrier or auxiliary agent. The invention comprises in particular a pharmaceutical preparation that contains the hormone of the invention in combination with other hormones, especially at least one gonadotropic hormone. The pharmaceutical preparation in accordance with the invention is preferably used to stimulate the proliferation of Leydig cells in those male subjects where the Leydig cells are damaged, e.g. after chemo- or radiation-therapy for tumors, especially testes-related tumors which cause androgen deficiency. Treatment with SIP could replace lifelong dependency on testosterone.

Further, a pharmaceutical preparation in accordance with the invention can be used for treating hypogonadotropic hypogonadism so as to improve spermatogenesis. To date, this has been accomplished by using hCG in combination with hMG. The administration of SIP could result in a rapid initiation of spermatogenesis, thus reducing the time interval until conception.

Further, it is possible to apply SIP either as a sole drug or, for example, in combination with hMG to increase the number of sperms when treating idiopathic oligoospermia.

In female subjects, SIP stimulates follicle growth and can therefore be used in treatments for the formation of multiple follicles, e.g. artificial insemination or in vitro fertilization. Further, SIP may serve as a replacement for Clomifen to induce ovulation. Sterile women, for example, who are resistant to Clomifen treatment must presently be treated with a combination of hMG and hCG. However, this therapeutic treatment is difficult to execute and can be dangerous since it may produce overstimulation which in few instances already led to the death of the patient. In this aspect, SIP is a safe drug.

In the so called "resistant ovarium syndrome," there is no stimulation of the follicles by FSH. The cause of this disease is not yet known although a deficiency of FSH receptors is believed to be involved. The hormone of the invention could also be used as a treatment for this disorder since its activity is not dependent upon FSH- nor LH-receptors.

This listing of therapeutic applications of the hormone SIP does not exclude the use of SIP in other therapeutical treatments where the production of the hormones in sex cells must be stimulated.

Finally, SIP can also be used in diagnostic procedures for the detection of functional disorders in sex cells. In female subjects, for example, where a follicle matures but ovulation does not occur, SIP cannot be detected. Also, by examining Leydig cells for ability to respond to SIP stimulation, it is possible to detect various causes of defects in Leydig cells, e.g. failure of the LH-receptor or the adenylate cyclase or mitochondrial defects.

DETAILED DESCRIPTION OF PREFERRED EMBODIMENTS

EXAMPLE 1

Insulation and purification of SIP.

1.1 Collecting human follicle fluid (hFF).

hFF was obtained from female subjects participating in an in vitro fertilization program conducted at the University of Münster. The female subjects were treated with human menopausal gonadotropin (hMG) and human chorionic gonadotropin (hCG) to induce follicle development and ovulation. Oocyte and follicle fluids were collected between 32 and 36 hours after administration of the hormones. The individual hFF-samples were centrifuged for 10 minutes at 1500 g to remove cellular components. The supernatants were collected and stored at −200° C.

1.2 Ammonium sulfate precipitation and dialysis.

The hFF-proteins were precipitated overnight at 4° C. with 80% ammonium sulfate. The precipitates were washed with an ammonium sulfate solution of the same concentration and solubilized in distilled water. The protein solutions were then dialyzed against phosphate-buffered saline solution (PBS) for 48 hours at 4° C. using a dialyzing membrane with a permeability limit of 10,000 D (Sigma Chemikalien). The dialyzed material was stored at −80° C. to further purify active substances.

1.3 Gel filtration with Sephadex G-75 and Ultrogel AcA 54 and gel chromatography with Sephacryl 2000.

Two successive columns were used to fractionate the hFF-proteins after ammonium sulfate precipitation and dialysis. The sample (10 ml) was applied onto a Sephadex G75 column (Pharmacia) of 2.5×90 cm, and the eluate was run on an Ultrogel ACA54 column (LKB) of 1.6×80 cm in size. The elution with 0.1 mol/liter Tris/HCl pH 7.4 was carried out at a speed of 6 ml/h and 2 ml fractions, where the optical density was determined at 280 nm, were collected every 20 minutes. Biological activity (stimulation of testosterone production in Leydig cells of the rat) was determined each time 5 fractions were collected.

Alternatively, 10 ml of dialyzed hFF proteins were separated on a Sephacryl S200 column of 2.5×80 cm in size using 20 mmol/liter Tris/HCl buffer, pH 7.1, 0.15 mmol/liter NaCl at a flow speed of 1.0 ml/min. The optical density was measured at 280 nm and 3.0 ml fractions of the eluate were collected. The individual fractions were examined for stimulation of steroid synthesis in Leydig cells.

1.4 Concentration of active fractions.

The bioactive fractions were concentrated by filtration with Amicon filters (CF3OA) with a molecular weight cut-off of 30 kD. The supernatants which contained the major portion of the bioactivity were used for further purification. As compared thereto, lyophilization led to a loss of bioactivity.

1.5 Affinity chromatography with Blue Sepharose.

After concentrating, the combined bioactive fractions were purified by affinity chromatography with Blue Sepharose (CL-6B; Pharmacia) using a Fast Protein Liquid Chromatography apparatus (Pharmacia). 5 ml of the sample were applied to a column of 1.0×30 cm using a super loop (Pharmacia). The column was rinsed at 1.5 ml/min using phosphate buffer (50 mmol/liter, pH 7.4). After eluting the non-bound proteins, the bound proteins were eluted with the aid of the same buffer, however, with an additional 2 mol/liter NaCl. The individual fractions (2.0 ml) were run on small Sephadex G-25 columns (PD 10; Pharmacia) to remove salts. All fractions were then tested for bioactivity.

1.6 Ion exchange chromatography with Mono S.

The combined bioactive fractions, after Sephacryl S-200 chromatography, were again purified on a cation exchange column (Mono S, HR 5/5; Pharmacia). The separation was carried out at pH 5 using 50 mmol/liter acetate as buffer A and the same buffer with 1.0 mol/liter sodium chloride as buffer B in accordance with manufacturer's instructions. All fractions were tested for bioactivity, and the active fractions were combined.

1.7 Ion exchange chromatography with Mono Q.

The active fraction obtained after step 1.5 were further purified in two steps on an anion exchange column (Mono Q, HR 5/5; Pharmacia) with the aid of an FPLC-apparatus. In accordance with the data supplied by the manufacturer, the first step included a buffer containing 20 mmol/liter Tris/HCl, pH 7.1, and 0.15 mol/liter NaCl, and a buffer B containing 20 mmol/liter Tris/HCl, pH 7.1, and 1.0 mol/liter NaCl.

The second purification step was carried out using the same buffer and the same program, except that the pH value of the buffer was 8.0. The individual fractions (1.0 ml) from these purification steps were run on Sephadex G-25 columns before being tested in bioassays.

1.8 Gel chromatography with Superose 12.

The active fractions of the Mono Q chromatography (pH 8.0) were concentrated and purified via gel chromatography with a Superose 12 column (HR 10/30; Pharmacia) with the aid of an FPLC-apparatus and PBS as an elution buffer. The elution was carried out at a speed of 0.5 ml/min and fractions of 1.0 ml were collected and subsequently tested for bioactivity.

EXAMPLE 2

Characterization of SIP.

2.1 Isoelectric focussing of the active fractions.

Figure 1:
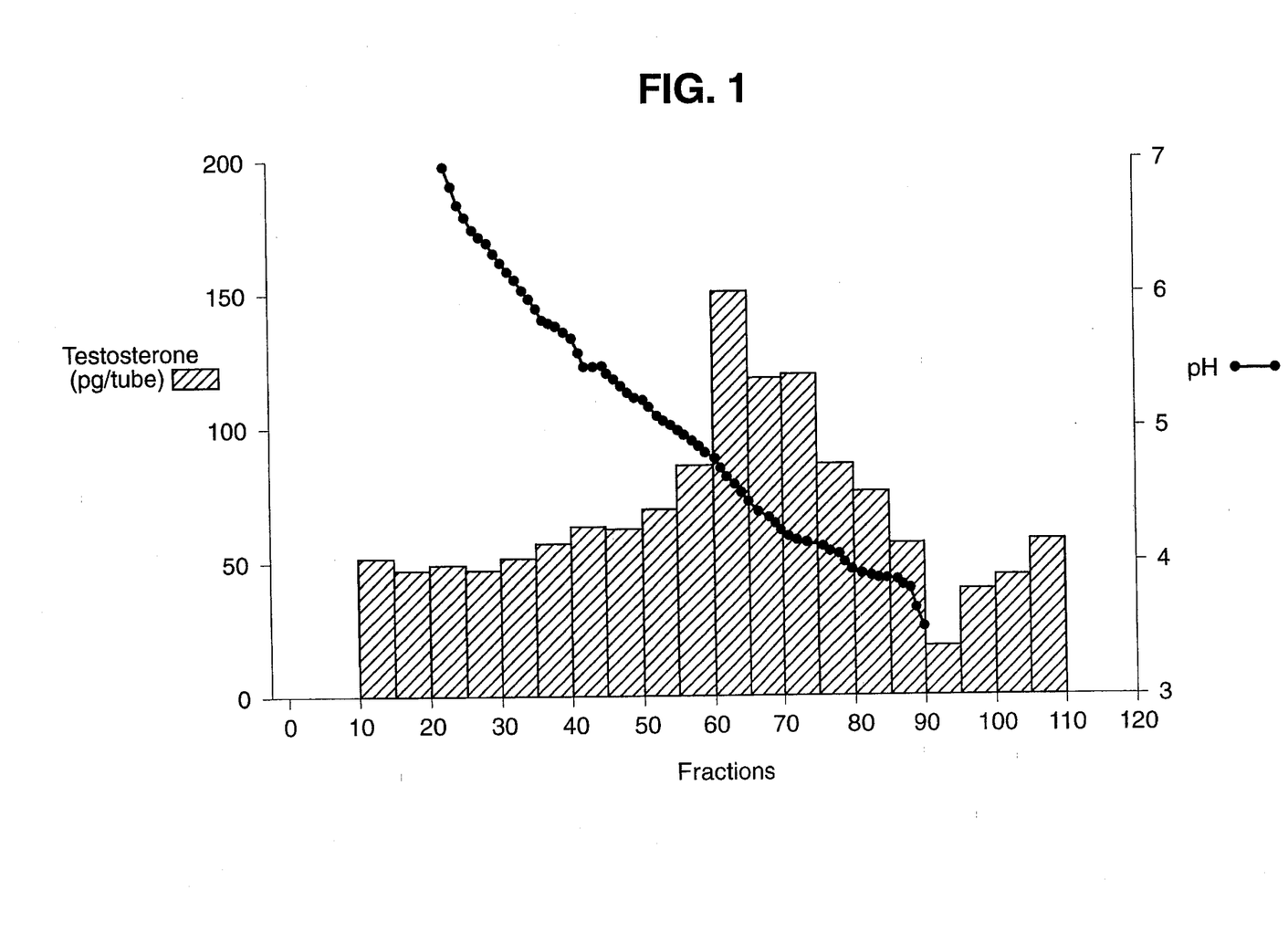
FIG. 1 shows the isoelectric focusing of the biological activity of human follicle fluid in a pH range of 3.5 to 7.0.

Isoelectric focussing on sucrose density gradients using a 110 ml glass column (LKB) was carried out according to Robertson and Diczfalusy (1977), Mol. Cell. Endocrinol. 9, 57–67. Ampholytes (Ampholine; LKB) were used in a concentration of 1% to produce a pH gradient ranging between 3.5 and 7.0. After running for 17 hours at 4° C., the fractions were collected from the bottom of the column and the pH-value of the individual fractions was determined. The fractions were then run on Sephadex G-25 columns (as described above) to remove ampholytes and sucrose. FIG. 1 shows the result of this isoelectric focussing. The bioactive fractions are in a pH-range between 4.5 and 5.5.

Then, isoelectric focusing was carried out with the aid of polyacrylamide gel (Phast-System, Pharmacia). The gels were prestained with Silver Stain in accordance with the instructions of the manufacturer.

2.2 SDS-PAGE.

In order to test the purity of the bioactive substance, SDS-PAGE was carried out under both reducing and non-reducing conditions. The gels were pre-stained with Silver Stain with the aid of the Phast system in accordance with the instructions of the manufacturer. The SDS-PAGE analysis of highly purified SIP under both reducing and non-reducing conditions showed only one band with a molecular weight of 60 kD.

EXAMPLE 3

Stimulating Testosterone Production in the Leydig Cells of a Rat.

3.1 Culture medium.

All incubation reactions with testicular tissue or isolated cells were carried out in a 1:1 mixture of Ham's F-12 growth medium and Dulbecco's modified Eagles Minimum Essential Medium (DMEM). The medium contained an additional 20 mmol/liter HEPES, 20 mmol/liter L-glutamine and 0.2% bovine serum albumin.

3.2 Leydig cells.

The testes of adult rats (60 days of age) were removed to obtain Leydig cell preparations. The skin of the testes was removed, and the tests were then incubated for 10–12 minutes in a medium with 0.25 mg/ml collagenase (type 1, Sigma Chemicals) being added. After the pellet had settled, the supernatant which contains the Leydig cells was collected. The Leydig cells were washed twice with the medium and at 32° C. incubated for one hour. The cells were then centrifuged for 10 minutes at 600 rpm, the supernatant was discarded and the pellet was resuspended in fresh medium.

3.3 Test for bioactivity.

200 µl of this cell suspension (inclusive of ca. $3 \times 10^4$ living cells) were incubated for 3 hours at 32° C. in the presence of the test substances. The testosterone content of the incubating medium was then determined by an RIA according to conventional methods. This test was also used routinely in purification processes for SIP (example 1).

Figure 2:
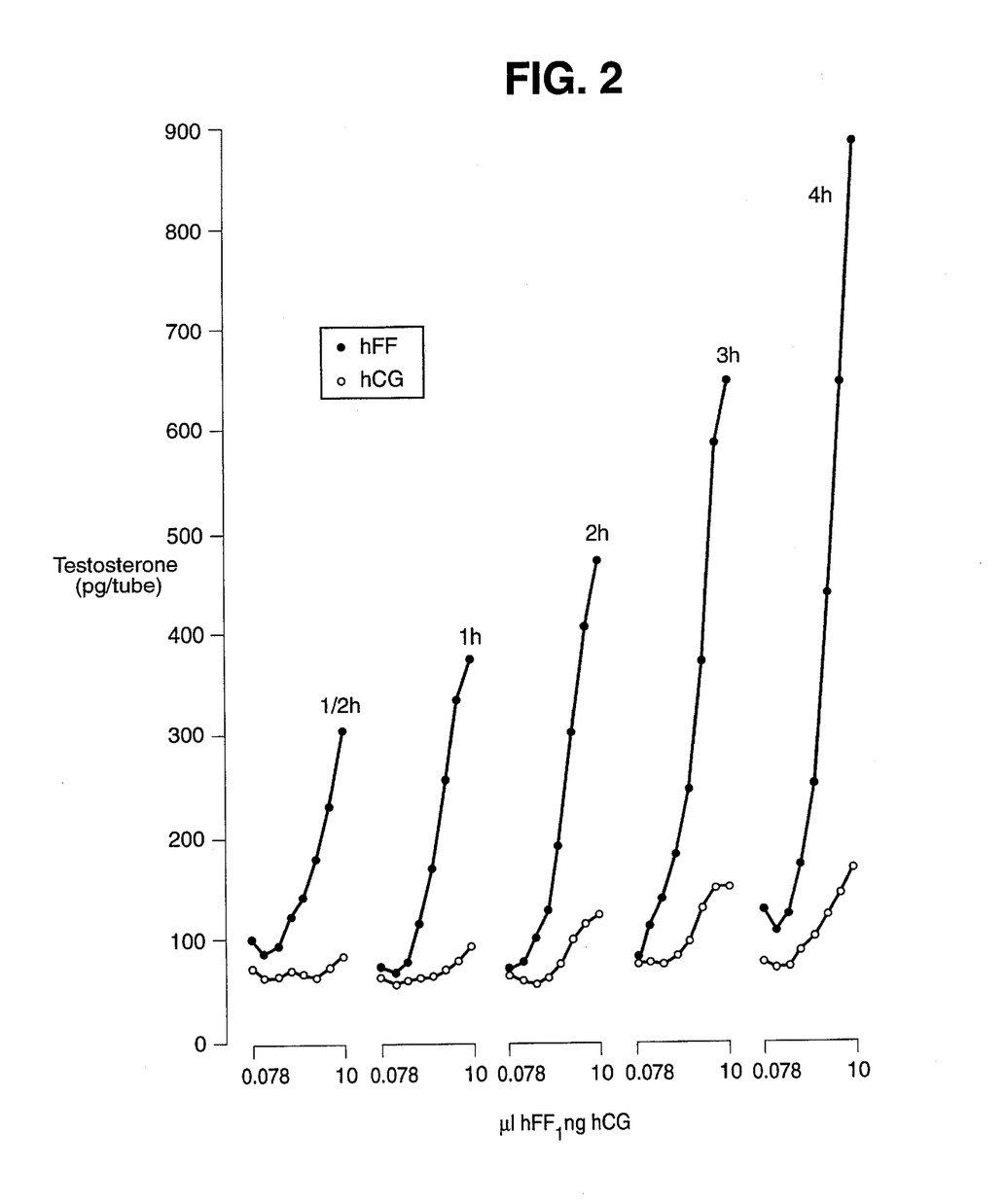
FIG. 2 is a comparison of the time-dependent effects of hCG and SIP on the testosterone production in Leydig cells of rats.

In order to detect the effect of hCG and SIP over time, the cells were incubated as described above for ½, 1, 2 and 4 hours, and the testosterone in the medium was determined. FIG. 2 is a comparison of the time-dependent effect of hCG and SIP (referred to as hFF-protein). The addition of hCG stimulated testosterone production only after 2 hours. The stimulating effect of the hFF-protein, as compared thereto, took effect after only 30 minutes of incubation and greatly exceeded the effect of hGC. It must therefore be assumed that both hormones stimulate steroidogenesis via different mechanisms.

When the cells are incubated with hFF-protein in the presence of maximum concentrations of hCG, cholera toxin and cAMP, SIP further stimulates testosterone production. Moreover, hCG triggers stimulation of cAMP production through the Leydig cells of the rat whereas SIP, under the same conditions, has no effect on the cAMP production. From this it can be inferred that SIP stimulates the production of steroids without the involvement of the cAMP cycle.

Further, SIP also stimulates testosterone production in Leydig cells of 10 days old. These cells were incubated with SIP for 24 hours before the culture medium was tested for testosterone.

EXAMPLE 4

Stimulation of Progesterone Production in Granulosa Cells.

4.1 Culture medium.

The medium described in 3.1, but containing 5% fetal bovine serum instead of bovine serum albumin and additional antibiotics (1300 mg/liter streptomycin, 600 mg/liter penicillin, and 10 mg/liter gentamicin) was used for a long-term culturing of human granulosa lutein cells.

4.2 Human granulosa lutein cells.

When oocytes were recovered from the ovaries, other cells from which follicle fluid was separated by centrifugation were also recovered. Granulosa lutein cells were separated from the pellets by centrifugation in 60% Percoll (Pharmacia), and the erythrocytes were removed. After washing, the granulosa cells were isolated by means of hyaluronidase treatment (0.1%, 20 minutes) and $6 \times 10^4$ living cells were cultured in a total volume of 1.0 ml (cf. Wickings et al. (1986), J. Reprod. Fert. 76, 677–684). The medium was replaced every 48 hours. The progesterone content of the culture medium was determined according to conventional methods by RIA using reagents that were obtained from the WHO Matched Reagents Programm.

4.3 Test for bioactivity.

Figure 3:
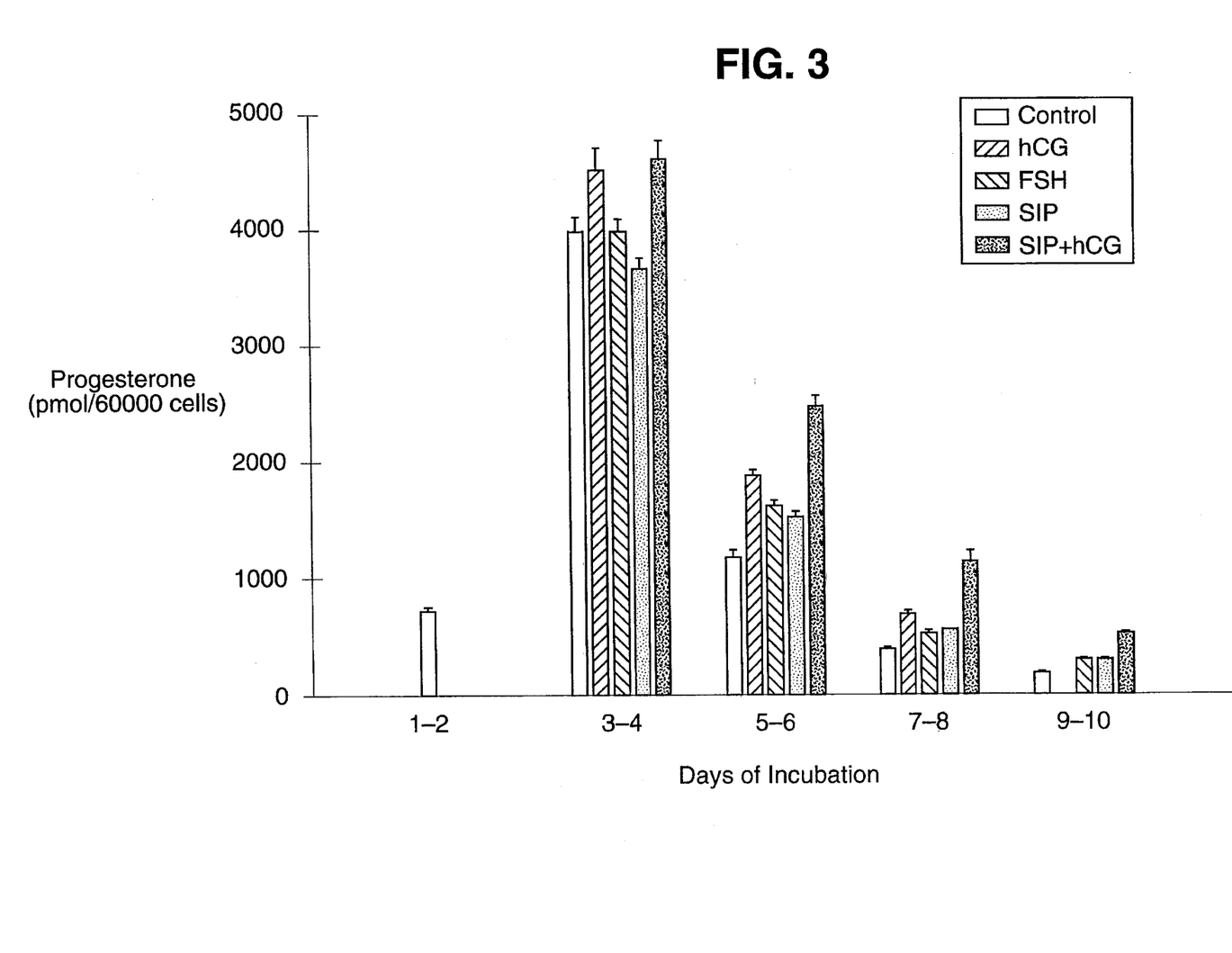
FIG. 3 is a comparison involving the effect of hCG, FSH and SIP on the progesterone production in human granulosa cells in vitro.

Highly purified SIP showed significant stimulation of progesterone production in human granulosa lutein cells in vitro. As seen in FIG. 3, it is clear that SIP is effective both alone and in combination with hCG.

EXAMPLE 5

Proliferation of Leydig Cells.

Leydig cells were obtained as described in example 3 from immature 20 day old rats. Approximately $0.25 \times 10^6$ living cells were spread in 24 culture dishes with 0.5 ml RPMI medium. After 24 hours of culturing, the medium was removed and fresh medium which contained the test substances was added. After 18 hours of incubation, 0.5 Ci $^3$H-thymidine were added, and the cells were cultured for four more days. After removing the medium, the cells were washed with 0.4 ml medium and frozen. In order to carry out the test, the cells were first sonified. Subsequently, the extracts were filtrated through DE81 Whatman filter paper. The radioactivity of the individual filter papers was measured in a scintillation counter.

Figure 4:
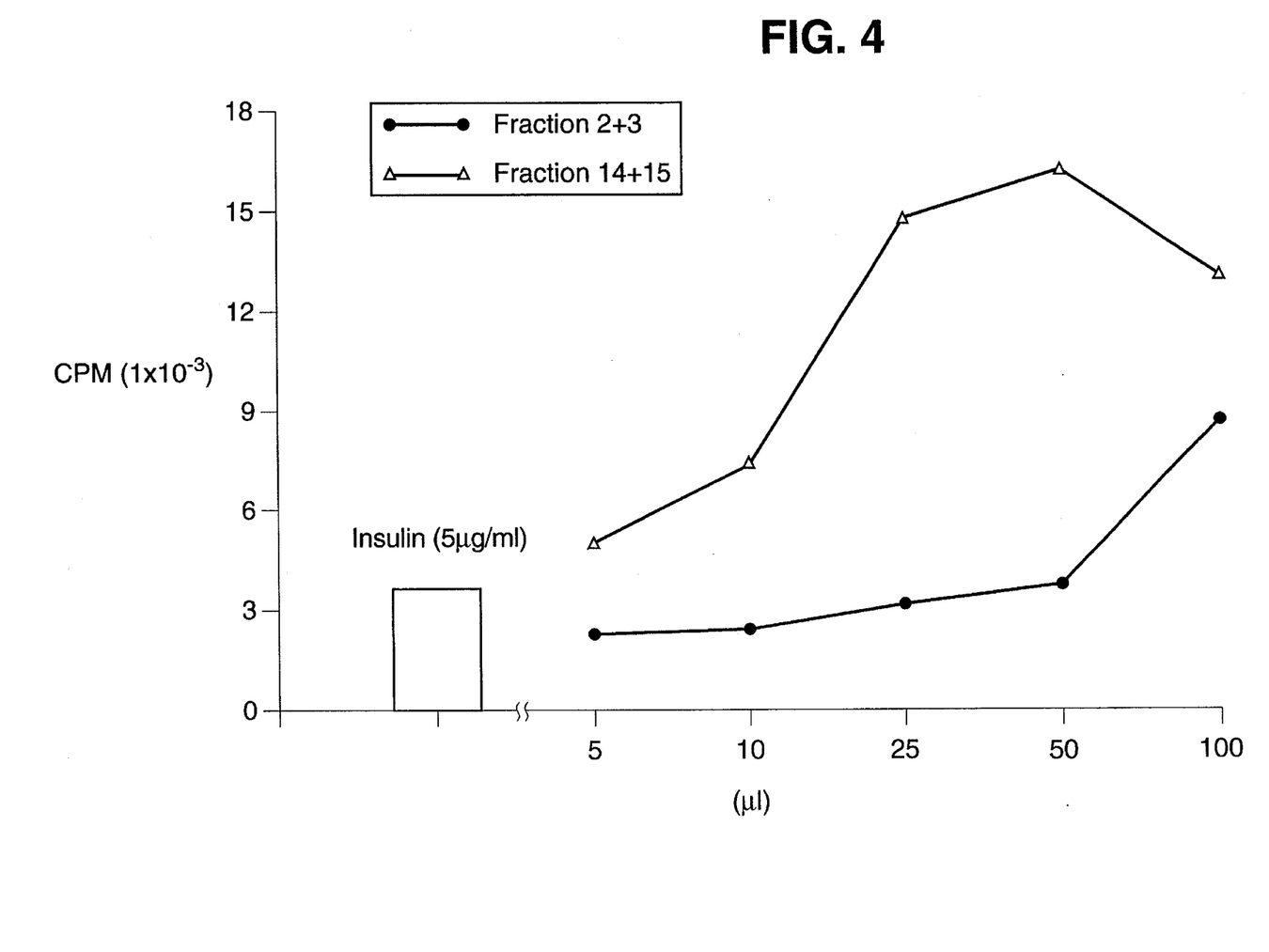
FIG. 4 shows how proliferation of immature Leydig cells of a rat is stimulated by SIP.

As seen in FIG. 4, purified bioactive hFF-fractions after Mono Q-chromatography show significant stimulation of the incorporation of $^3$H-thymidine in immature Leydig cells. From this, it can be inferred that SIP stimulates the proliferation of rat-Leydig cells in vitro. This stimulation is specific to Leydig cells since the same fractions do not cause proliferation of granulosa cells and mouse thymocytes.

EXAMPLE 6

Stimulation of Cholesterol Side Chain Cleavage by SIP.

Figure 5:
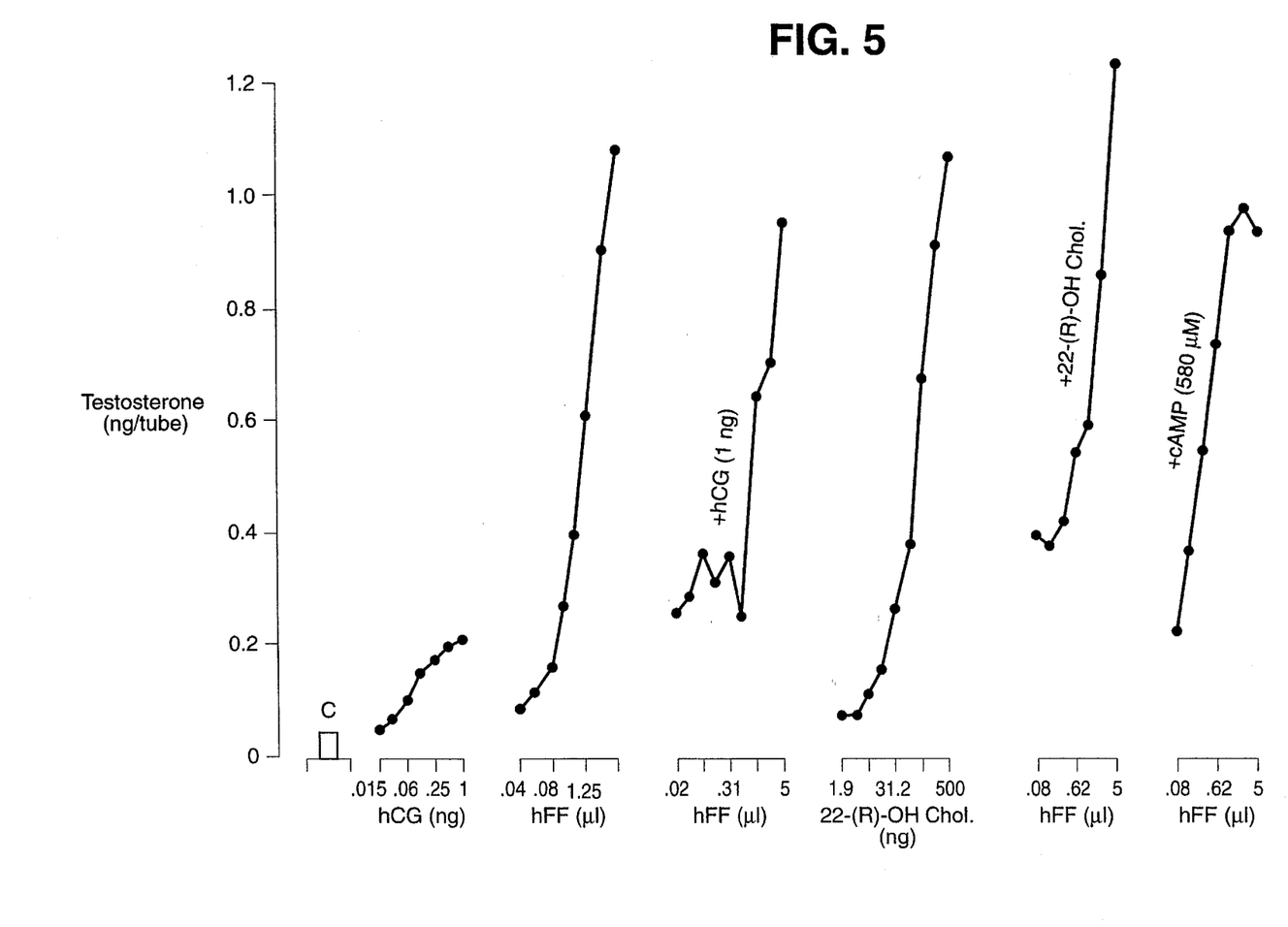
FIG. 5 is a comparison of the effects of hCP, SIP and 22-R-OH-cholesterol on testosterone production of Leydig cells of rats.

FIG. 5 shows the effects of 22-R-OH cholesterol and SIP are very similar with respect to testosterone production in Leydig cells of rats (cf. example 3). When steroid production is stimulated by 22-R-OH cholesterol, SIP even exhibits synergistic activity.

It is known that the stimulation of testosterone production by 22-R-hydroxy cholesterol by bridging the cleavage of cholesterol side chain occurs with the participation of mitochondrial Cytochrome P450 (Rommerts et al. (1986), J. Endocrinol. 109, 111–117). From the similar effects of 22-R-hydroxycholesterol and SIP, it can be inferred that SIP, on the level of mitochondria, also stimulates testosterone synthesis by stimulating cholesterol side chain cleavage.

EXAMPLE 7

Steroidogenesis in Adrenal Cells.

Figure 6:
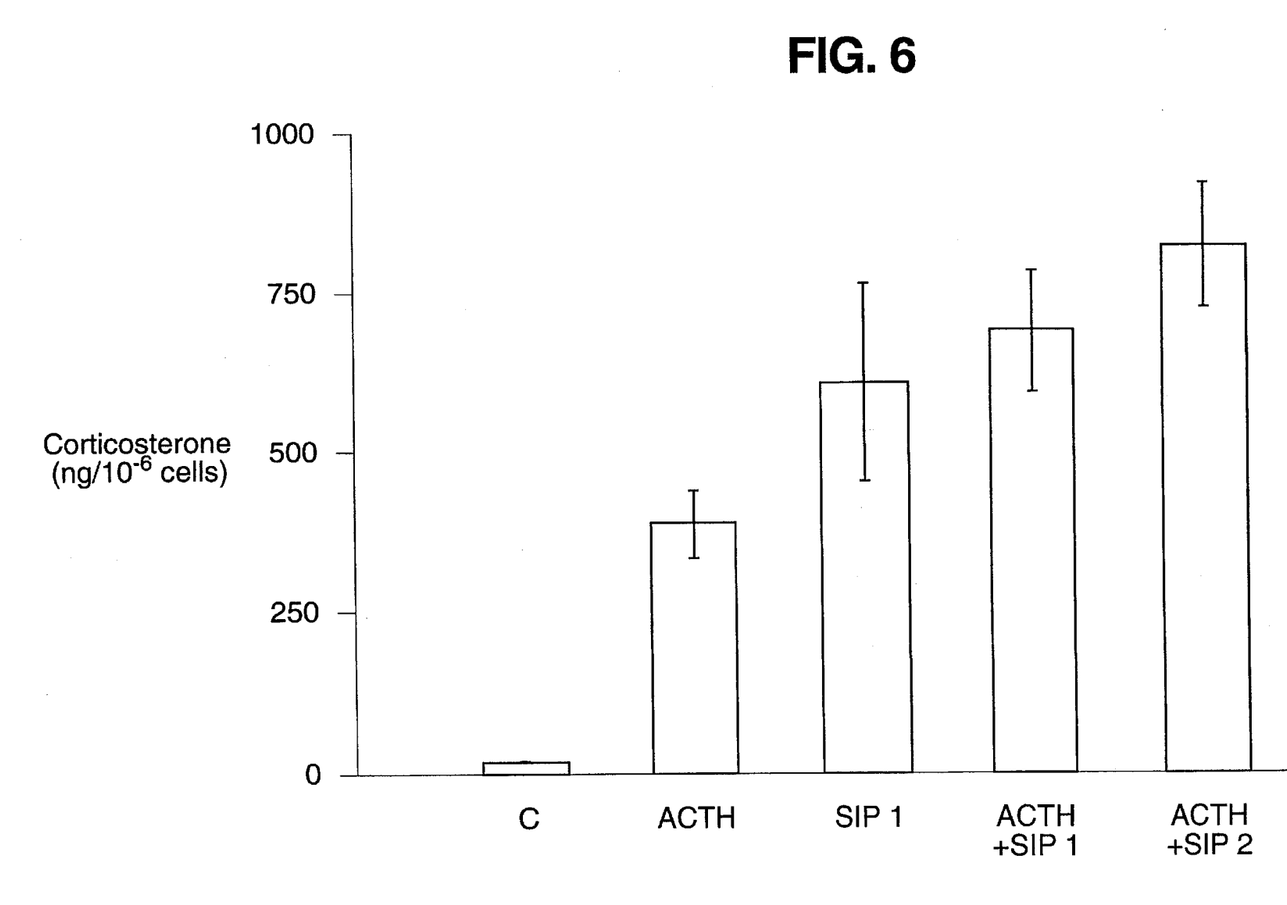
FIG. 6 shows the effects of SIP on the in-vitro formation of corticosterone by adrenal cells of the rat.

Adrenal cells were obtained from glands that were isolated from male rats in accordance with the method of Ray & Scott in Endocrinology 103: 1281. Approximately 5×10$^5$ living cells were incubated in a metabolic shaker at 37° C. for 3 hours with and without test material. The incubation media were analyzed for corticosterone with the aid of an radioimmunoassay kit (RSL$^{125}$I Corticosterone-kit by ICN Biomedicals, Inc. Carson, Calif., U.S.A.). The cells were incubated either solely with 40 µg SIP or in combination with maximum concentrations of ACTH (25 mIU Synacthen) and one db cAMP (25 µg). The results are shown in FIG. 6. Each bar represents the average of two independent experiments. As seen in this Fig., SIP induces both basal and ACTH- or cAMP-stimulated steroid production. The stimulation by SIP is also seen in the presence of maximum concentrations of ACTH and cAMP.

It will be understood that the specification and examples are illustrative but not limitative of the present invention and that other embodiments within the spirit and scope of the invention will suggest themselves to those skilled in the art.

I claim:

1. Substantially pure steroidogenesis inducing protein (SIP) characterized by a molecular weight of 60 kd as determined by SDS-PAGE, and an isoelectric point of from 4.7 to 4.9, wherein said SIP stimulates production of sex cells and adrenal cells via a mechanism which does not involve cAMP.

2. Pharmaceutical composition useful in stimulating production of sex cells and adrenal cells comprising the substantially pure steroidogenesis inducing protein of claim 1 and a pharmaceutically acceptable carrier.

3. Pharmaceutical composition of claim 2, further comprising at least one additional gonadotropic hormone.

4. Method for stimulating steroidogenesis comprising administering an amount of the substantially pure steroidogenesis inducing protein of claim 1 to a subject in need of increased steroidogenesis, in a steroidogenesis stimulating effective amount.

5. Method of claim 4, comprising administering said substantially pure steroidogenesis inducing protein to a subject with hypogonadotropic hypogonadism.

6. Method of claim 4, comprising administering said substantially pure steroidogenesis inducing protein to a subject with idiopathic oligozoospermia.

7. Method for stimulating proliferation of Leydig cells comprising administering an amount of the substantially pure steroidogenesis inducing protein of claim 1 to a subject in need of increased Leydig cell proliferation in an amount sufficient to stimulate Leydig cell proliferation.

8. Method of claim 4, wherein said stimulation of steroidogenesis comprises increased production of progesterone.

9. Method of claim 4, wherein said stimulation of steroidogenesis comprises increased production of testosterone.

* * * * *